United States Patent [19]
Carpentier et al.

[11] Patent Number: 5,961,550
[45] Date of Patent: Oct. 5, 1999

[54] HEART VALVE ACTIVATING SYSTEM AND ACTIVATED HEART VALVE

[75] Inventors: Alain Carpentier, Paris; Vincent Garitey, Voiron; Michel Hassler, St. Ismier, all of France

[73] Assignee: Societe Industrielle De Combustible Nucleaire-sicn, France

[21] Appl. No.: 08/894,513

[22] PCT Filed: Feb. 20, 1997

[86] PCT No.: PCT/FR97/00312

§ 371 Date: Aug. 21, 1997

§ 102(e) Date: Aug. 21, 1997

[87] PCT Pub. No.: WO97/30658

PCT Pub. Date: Aug. 28, 1997

[30] Foreign Application Priority Data

Feb. 20, 1996 [FR] France .................. 96 02052

[51] Int. Cl.⁶ .................................................. A61F 2/24
[52] U.S. Cl. .................................................. 623/2; 251/65
[58] Field of Search .................................. 623/2; 251/65

[56] References Cited

U.S. PATENT DOCUMENTS

| 3,370,305 | 2/1968 | Goott et al. ................................ 623/2 |
| 3,794,854 | 2/1974 | Kurpanek . |
| 3,959,827 | 6/1976 | Kaster ......................................... 623/2 |
| 4,245,358 | 1/1981 | Moasser ...................................... 623/2 |
| 4,605,408 | 8/1986 | Carpentier . |
| 4,657,545 | 4/1987 | Zibelin ....................................... 623/2 |
| 4,979,955 | 12/1990 | Smith ......................................... 623/2 |
| 5,135,538 | 8/1992 | Pawlak et al. ............................. 623/2 |

FOREIGN PATENT DOCUMENTS

| 3128704 | 2/1983 | Germany . |
| 608368 | 1/1979 | Switzerland . |

*Primary Examiner*—Paul B. Prebilic
*Attorney, Agent, or Firm*—Ostrolenk, Faber, Gerb & Soffen, LLP

[57] ABSTRACT

An activating system is provided for a heart valve having a seat (1) and at least one pivoting flap (2a, 2b) mounted on the seat (1). The activating system includes at least one mobile magnetic element (4) connected with said flap (2a, 2b) and at least one fixed magnetic element (3) on the seat (1), with the magnetic elements (3, 4) producing interacting fields that create a force which is exerted on said flap (2a, 2b) during its opening and/or closing movements.

23 Claims, 14 Drawing Sheets

HEART VALVE ACTIVATING SYSTEM AND ACTIVATED HEART VALVE

This application is a national stage application under 35 U.S.C. 371 of PCT/FR97/00312 filed Feb. 20, 1997.

The present invention relates to a heart valve activating system and to an activated heart valve.

Artificial heart valves, also known as mitral or aortic prostheses, generally consist of one or two mobile flaps mounted on a seat by means of one or more joints, said seat also being sutured to the patient's natural ducts.

In the working cycle of the valves, the flap opening and closing phases are of very short duration compared with the phases corresponding to blood flow or blocking. Nevertheless, the quality of an artificial heart valve is determined largely by these opening and closing phases, and the precise moment at which they take place in the cardiac cycle.

Generally when an artificial valve is closed and when the pressure difference on either side of the valve orifice inverts, the force which was keeping the flaps closed changes direction and tends to open them. This force, and hence the pressure difference which generates it, have to reach a sufficient level to start the opening of the flap or flaps and simultaneously to initiate blood flow through the prosthesis. The closing of an open mechanical valve which is allowing the blood to flow through takes place when pressure difference on either side of the valve orifice inverts and increases and then ultimately causes a reversal blood flow. This reverse flow then closes the valve by moving its flaps.

In summary, a traditional mechanical valve operates with a delay relative to the pressure fluctuation because a significant pressure difference has to be established before flap movement is initiated. Furthermore, the opening and closing mechanisms of the traditional artificial valves are identical, whether implantation is at the aortic or mitral position, which is not the case for natural valves.

The opening and closing mechanisms of natural valves are such that the natural aortic valve opens at the same time as the ventriculo-aortic pressure difference inverts. This is because a natural aortic valve has no inertia so that it opens under a zero pressure difference, in contrast to delayed operation for a mechanical valve prosthesis. At the end of the systole, the natural valve closes gradually, but rapidly and without reverse flow, under the action of local pressure differences on the lamellae, which are equivalent to the flaps. These local pressure differences precede the overall inversion of the pressure difference between the aorta and the ventricle, said inversion being necessary for initiation of reverse flow. It is for this reason that the natural aortic valve closes without reverse flow at the moment when the aortic pressure becomes greater than the ventricular pressure, whereas it is the reverse flow which closes a mechanical valve prosthesis.

The natural mitral valve actively opens under the effect of the tension of cords attached, on the one hand, to the edges of its lamellae and, on the other hand, to the inner walls of the ventricle. It is the dilation of the ventricle during the diastole which simultaneously causes the drop in ventricular pressure (and hence the inversion of the auriculo-ventricular pressure difference) and the opening of the mitral valve by traction on its cords. Therefore opening of the natural mitral valve is strictly synchronous with the inversion of auriculo-ventricular pressure, whereas a mechanical valve prosthesis opens with a delay because a pressure difference is required in order to open. The closing of the lamellae of the natural mitral valve takes place due to the simultaneous occurrence of several events, particularly, the cords holding the lamellae relax, the lamellae gradually close under the action of local pressure differences (preceding the overall inversion of the pressure difference between the atrium and the ventricle), and the mitral valve orifice contracts (bringing the lamellae closer together). Thus, like the natural aortic valve, the natural mitral valve closes without reverse flow. This is in contrast to an artificial valve, in which the flap or flaps are moved throughout their closing phase by the reverse flow of fluid.

The flaps of artificial valves therefore have a degree of inertia and both their opening and their closing require an expenditure of energy taken from the energy of the blood that is flowing. It is clear that this energy which is produced by the heart, and then communicated to the blood flows, will have to increase with the pressure loss across the valve and with the magnitude of the reverse blood flow through the valve when it closes. The extra effort thus generated by the heart penalizes the patient, particularly in the case of the mitral valves, where the rates and hence energies of the already naturally weak blood flows are even weaker in the presence of pathological heart conditions. If it is desired to reduce the pressure loss across the valve, the flaps can be given a maximum opening capacity with large amplitudes of displacement, but this then results in an increase in the reverse flow during the necessarily extended closing phase. Conversely, if it is desired to reduce the reverse flow by decreasing the opening and closing stroke of the flaps, the pressure loss across the valve is increased.

At a high rate, some valve prostheses experience a prohibitive increase in the ratio of the reverse flow volume to the output volume (because the duration of the reverse flow required to close the flaps tends to occupy a large part of the cycle). In the case of valve prostheses with several flaps, one of the flaps may not open, causing thromboses. This can happen in particular when the patient has a pathological heart condition of low output and/or adopts a substantially horizontal position.

Furthermore, the blood flows at the heart orifices are not necessarily symmetrical, which may cause the conventional valve prostheses to operate asymmetrically. Such a mode of operation can jeopardize the integrity of the valve prosthesis because of the poor distribution of the stresses which are being experienced.

Also, in the traditional artificial valves, the flaps move directly from a fully open position to a closed position, which requires large and sudden displacements of the flaps and sometimes causes rupture or premature wear of the valve, as well as the generation of noise and cavitation.

All these disadvantages associated with the intrinsic nature of all the existing mechanical valve prostheses go a long way towards explaining the complications encountered in patients fitted with a valve prosthesis, namely excessive pressure loss and thromboembolic incidents. The latter are particularly frequent in the mitral position when the natural mitral valve with active opening is replaced by a valve prosthesis with passive opening. In fact, equipped with two flaps, the prosthesis can open asymmetrically, particularly if the patient has a low output, a condition that increases the risk of thrombosis.

The primary object of the instant invention is to solve the above problems or at least alleviate them in a satisfactory manner.

According to the invention, this object is achieved by means of a heart valve activating system comprising a seat and at least one pivoting flap mounted on the seat characterized in that it comprises at least one mobile magnetic element on the flap and at least one fixed magnetic element integral with the seat, said magnetic elements creating a force which is exerted on said flap during its opening and/or closing movements.

In one particular embodiment, said mobile magnetic element produces a first magnetic field and said fixed magnetic element produces a second magnetic field, with these magnetic fields being determined in such a way that, when the blood pressure is identical on either side of the valve, their reciprocal influence establishes an equilibrium position towards which the mobile magnet and flap are returned at all timed by the net force of the magnets, which varies as a function of the position of said flap so as to minimize reverse blood flow without increasing pressure loss across the valve.

This equilibrium position preferably corresponds to an intermediate open position of the flap.

According to one advantageous characteristic, the variations in said force as a function of the position of the flap are independent on either side of the equilibrium position.

According to another characteristic, said force produces a magnetic torque exerted on the flap, the maximum value of which is between $10^{-3}$ and $10^{-5}$ Newton meters (N.m.). This torque is less than the forces exerted by the blood on the flap in its fully open position and closed position.

According to other advantageous characteristics of this invention, the first and second magnetic fields are determined in such a way that the flap pivots in the seat with the minimum of friction, and the equilibrium position is preferably situated between the fully open position and closed position.

Moreover, the reciprocal influence of the first and second magnetic fields produces repelling magnetic forces between the mobile magnetic element and the fixed magnetic element.

These repelling magnetic forces have an intensity of at most $10^{-1}$ N.

In a first embodiment, the fixed magnetic element is integrated into the thickness of the seat, for example near a joint. This arrangement makes it possible to avoid all contact with the blood. In the same way, the mobile magnetic element is integrated into the thickness of the flap and is enclosed in a leaktight manner, again making it possible to avoid all contact with the blood. These arrangements enable the activating system of the invention to be rendered biocompatible and, in particular, hemocompatible.

In general, the flap is made form a block of hemocompatible material which enables magnets to be incorporated without modification of their magnetic characteristics.

In another embodiment, the system comprises one mobile magnetic element and two or three fixed magnetic elements for each flap joint. In this case the fixed magnetic elements are preferably arranged in a ring around an axis of articulation of the flap.

In yet another embodiment, said magnetic elements are so-called rare earth permanent magnets based on samarium and cobalt or based on neodymium, iron and boron.

A further subject of the invention is a heart valve equipped with the activating system described above.

One particular embodiment of such a valve consists in machining a flap, made from a block of hemocompatible titanium alloy, to form a housing, placing the mobile magnetic element in this housing, closing off this housing with a cap made of the same titanium alloy, and finally welding this cap hermetically to the flap.

An alternative construction consists in making the flap of any material and then completely covering said flap with a hemocompatible material.

A first modified embodiment of the valve of the invention consists in providing it with two flaps activated only by the reciprocal influence of the mobile magnetic elements of each flap.

A second modified embodiment consists in making at least one of the two flaps or one of the two seats of a ferromagnetic material so as to form at least one mobile or fixed magnetic element which does not produce a magnetic field, but which is under the influence of the magnetic field or fields produced by the other mobile or fixed magnetic elements.

Another modified embodiment consists in providing the valve only with mobile magnetic elements, the seat then having no magnetic element.

Yet another modified embodiment consists in making provision for the presence of interactive mobile magnetic elements and the presence, on the seat, of fixed magnetic elements which are inactive or whose influence is negligible.

By virtue of the intermediate open position of the flap obtained when the pressures on either side of the valve are at equilibrium, the activating system of the invention allows active opening of the valve, in particular in the mitral position, guaranteeing symmetrical opening of all the flaps, even in cases of very weak blood flow, and makes it possible to reduce the reverse flow when the valve closes. The guarantee that all the flaps will open reduces the risks of thrombus formation.

The valves equipped with these activating systems are controlled by the variations in blood pressure and not by the flow rates, as is the case with passive valves, i.e. valves not activated according to the principle of the invention. Because the flow rate is itself generated by the pressure variations, it is possible to have opening and closing phases which are anticipated by comparison with the operating sequences of non-activated, traditional artificial valves. Consequently the flaps of the activated valves appear to have no inertia for the blood flows, which thus retain all their acquired energy.

The activating system of the invention also makes it possible to improve the efficiency of the valves by reducing reverse blood flow. In fact, magnetic assistance provided by the activating system causes the anticipated closure of the flap while the velocity of the reverse blood flow is still virtually zero. Jets which are produced at the moment of closure when the latter takes place in the presence of a significant velocity of reverse flow (as is the case with non-activated valves) generally entail risks of cavitation and hemolysis, which are therefore limited by the use of the invention.

It is acknowledged that the transitory phases of blood flow are accompanied by sudden pressure variations causing the opening or closing movements. Anticipation of the opening and closing movements relative to the reversals of flow at the valve orifice therefore enables the flap to perform its movement under low loads. This contrasts with passive valves, whose flaps withstand high loads, especially at the end of the stroke. Moreover, the proportion of the stroke of the flap which takes place under a high pressure difference is shorter than with non-activated valves, thereby limiting wear reducing shocks. This same anticipation makes flap movements symmetrical because identical magnetic torques initiate the movements of the flaps. Consequently, as the movements of the flaps are symmetrical, the distribution of stresses is symmetrical, favoring the fatigue strength of the active valve prosthesis.

The opening and closing movements have a first phase, which takes place under the impetus of magnetic forces, and a second phase, which is under the influence of hydraulic forces. Thus automatic return of the flaps to the intermediate open position of equilibrium also makes it possible to break up the movements and to reduce the velocities at the end of the opening and closing movements. This eliminates violent shocks on the seat, thereby reducing the risks of rupture, noise, cavitation and hemolysis.

The activating system of the invention allows a greater opening of the flap to reduce the pressure loss across the valve, without increasing the reverse flow by virtue of anticipating the movement when the valve closes.

Magnetic activation of the valve has particularly important effects, especially in the phases of the cardiac cycle in which the hydraulic forces are weak, i.e. between the diastole and the systole and, conversely, between the systole and the diastole. The intensities of the torques and magnetic forces in play can remain low while at the same time being effective, so they are not capable of perturbing the hydraulic operation of the valve during the diastolic and systolic phases. Thus, the magnitudes of these torques are not capable of causing any increase in pressure loss across the valve when the valve is open, any more than an increase in the leakage rate across the valve when the valve is closed.

The invention will be understood more clearly from the following description accompanied by the drawings, in which.

Figure 1E:
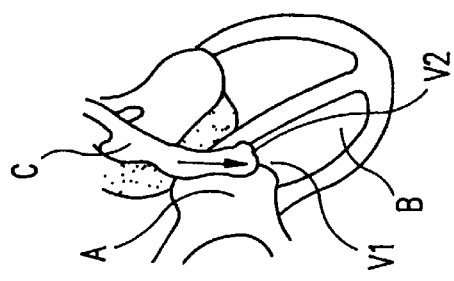
FIGS. 1a to 1e show schematic cutaway views of the heart during the different phases of the cardiac cycle.
Figure 1D:
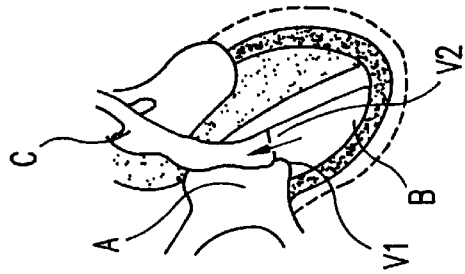
Figure 1C:
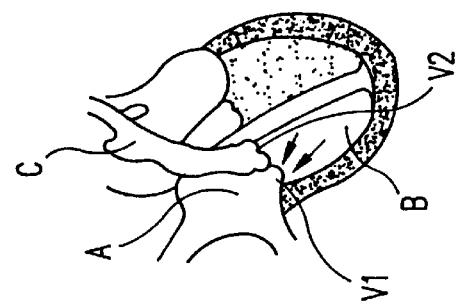
Figure 1B:
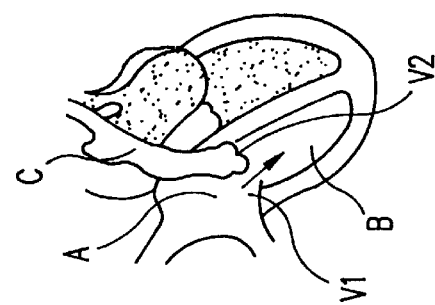
Figure 1A:
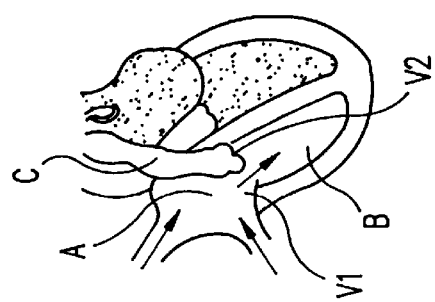

FIGS. 1a to 1e show the different phases of the cardiac cycle. Blood behaves like all fluids and always flows from a zone of high pressure to a zone of low pressure, thereby generating a flow rate. The cardiac contraction places the blood under pressure and the valves direct the blood flow that is generated by cardiac contraction. The variations in pressure and flow rate which appear during the cardiac cycle are shown for the left heart in FIGS. 2a and 2b. The behavior of the right heart is qualitively identical to that of the left heart. The systole corresponds to the period of ventricular contraction (FIGS. 1c and 1d), while the diastole corresponds to the period of relaxation (FIGS. 1a and 1b).

The following description pinpoints where the above-described opening and closing movements of the aortic and mitral valves are positioned in the cardiac cycle.

During the start of the diastole (FIG. 1a) the left atrium A is relaxed and the left ventricle B begins to dilate. This dilation causes the mitral valve V1 to open early due to traction on the cords. As the pressure in the atrium becomes greater than that in the ventricle, the blood passes from the atrium A into the ventricle B. During this time the aortic valve V2 is closed because the pressure in the aorta C is higher than in the ventricle B. However, the aortic pressure falls slowly when the ventricular pressure rises slightly. At the end of the diastole (FIG. 1b) the atrium A contracts so as to inject an additional volume of blood into the ventricle B.

Figures 2A, 2B:
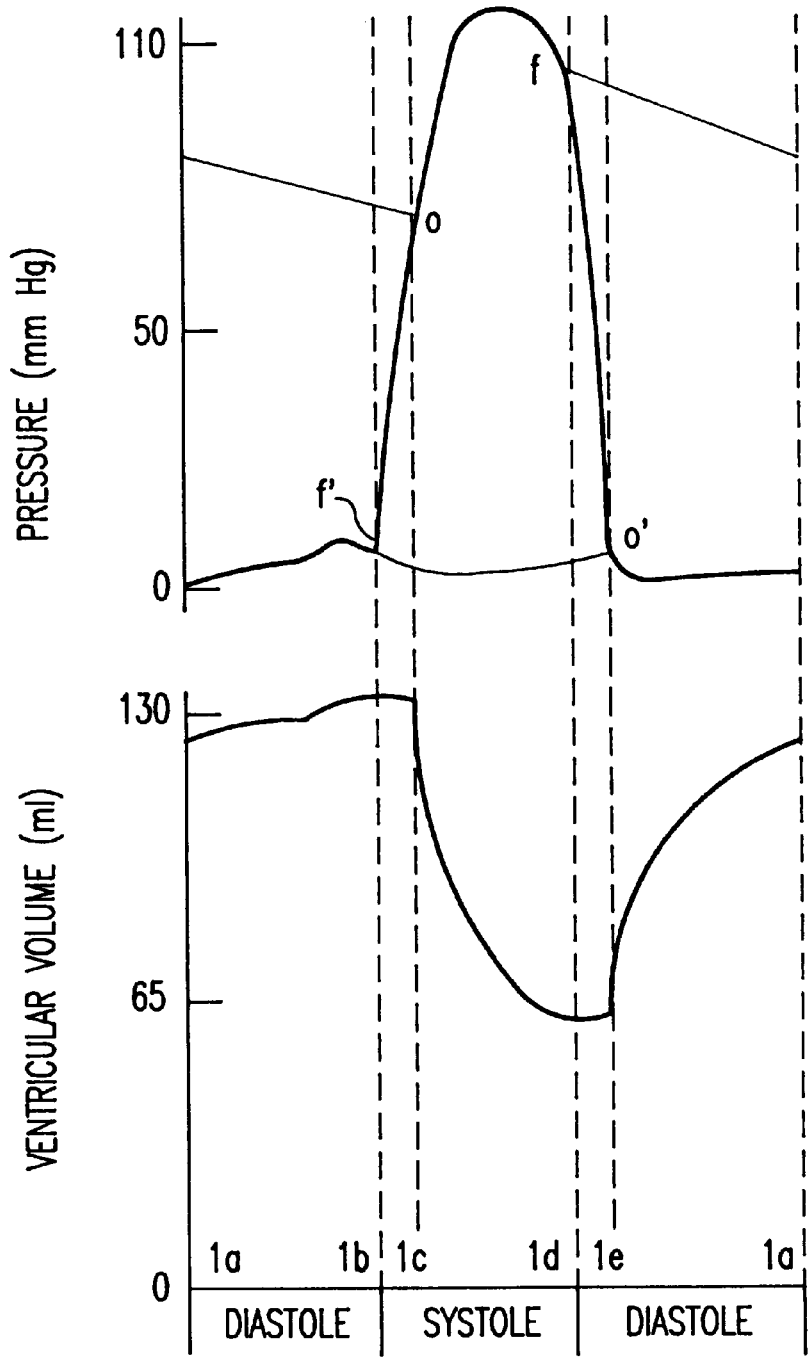
FIGS. 2a and 2b are graphs showing, respectively, the variations in pressure and the variations in ventricular volume during the cardiac cycle for the left heart.

Then the systolic phase starts and the ventricle B begins to contract, compressing the blood it contains. The ventricular pressure therefore increases very suddenly, almost immediately exceeding the auricular pressure. This causes the closure of the valve V1, facilitated by the equally sudden relaxation of the tension on the cords (FIG. 1c and point f in FIG. 2a). Reverse blood flow towards the atrium A is then no longer possible. Moreover, because of the fact that for a brief period the aortic pressure still exceeds the ventricular pressure, the aortic valve V2 remains closed. Then the ventricular pressure exceeds the aortic pressure, the valve V2 opens and ventricular ejection takes place (FIG. 1d and point O in FIG. 2a). As blood flows into the aorta C, the aortic pressure increases, but the ventricle B does not empty completely and the maximum aortic pressure is reached before ejection has ended. The flow rate of blood leaving the ventricle B during the terminal phase of the systole is low and is less than the flow rate of blood leaving the aorta. At the same time the auricular pressure also increases, slowly, throughout the ejection period. Then the ventricle B relaxes and the ventricular pressure falls below the aortic pressure, causing the aortic valve V2 to close (point f, FIG. 2a). However, the ventricular pressure, which is decreasing, is still greater than the auricular pressure, so the auriculo-ventricular valve V1 remains closed (FIG. 1e). When the left ventricle begins to dilate at the same time as the ventriculo-auricular pressure inverts, the valve V1 opens (point O', FIG. 2a) and the ventricle begins to fill again as described above in connection with the start of the diastole (FIG. 1a).

FIGS. 2a and 2b respectively show the variations in pressure and ventricular volume during the different phases described above with reference to FIGS. 1a to 1e, as marked at the bottom of FIG. 2b. It is fairly apparent from studying the cardiac cycle that the natural valves are synchronized with the relative pressures prevailing in the atrium, the ventricle and/or the aorta, and not with the flow rates. These valves therefore have opening and closing modes which are anticipated relative to the variations in flow rates. Also, the opening of the mitral valve V1 is facilitated by the ventricular dilation, which is accompanied by traction on the tendinous cords.

The objective (of the activating system) of the instant invention is to provide an activating system which causes artificial heart valves to operate according to opening and closing modes which are very similar to operational modes of natural valves. The valve 99 shown in FIGS. 3a, 3b and 3c et seq. is an artificial valve equipped with the activating system of the invention.

This valve 99 comprises a seat 1 and at least one flap, in this case two identical flaps 2a, 2b mounted on the seat 1 in symmetrical arrangement relative to the diametral axis XX'. Each of the flaps 2a, 2b pivots about an axis YY', parallel to and near the axis XX', by means of two symmetrical joints located on either side of each flap. A joint consists, for example, of a transverse finger 10 integral with the inner lateral face of the seat 1. Finger 10 is intended to fit, with freedom of relative rotation, inside a cylindrical cavity 20 created in the thickness of the lateral edge of the flap 2a, 2b or in an attached boss 21.

In the embodiment of the valve 99 shown, the two flaps 2a, 2b are moving into the closed position (FIGS. 3a to 3c), butting against one another with their respective inner edges 22a, 22b orientated along the axis XX'. For this purpose the inner edges 22a, 22b are chamfered so that, in the closed position, the flaps 2a, 2b form an angle 2β of between 90° and 180° with one another. The open position here is fixed at angle α=85° (cf. FIG. 8) relative to the basal plane S of the seat 1.

For each joint the actual activating system comprises at least one, and in the embodiment shown three, fixed magnetic elements 3 integral with the seat 1, and at least one mobile magnetic element 4, carried here by the flap 2a, 2b. The magnetic elements 3, 4 are suitable and intended for creating a force which is exerted on the flap 2a, 2b during its opening and/or closing movements.

In the embodiment shown in the Figures of the drawings, the fixed magnetic elements 3 and mobile magnetic element 4 respectively produce a first and a second magnetic field whose inherent characteristics may be different. These magnetic elements 3, 4 are preferably so-called rare earth permanent magnets (for example based on samarium and cobalt or based on neodymium, iron and boron) which have strong magnetizations and coercivities and hence a high magnetic stability.

The fixed magnetic elements 3 are sufficiently compact to be integrated into the thickness of the outer face of the seat 1, so they are not capable of coming into contact with the blood. The fixed magnetic elements 3 can be arranged in a ring, as illustrated especially in FIG. 3b, but they can have any other arrangement favorable to obtaining the desired magnetic fields. The first and second magnetic fields are determined so as to produce repulsive magnetic forces between the mobile element 4 and the fixed element 3. These forces have an intensity of between 0 and $10^{-1}$ N, and make it possible to both control the pivoting of each flap 2a, 2b and to center said flap in the seat, assuring a minimum of friction in particular. The mobile magnetic element 4 is integrated into the thickness of the flap 2a, 2b.

Figure 3A:
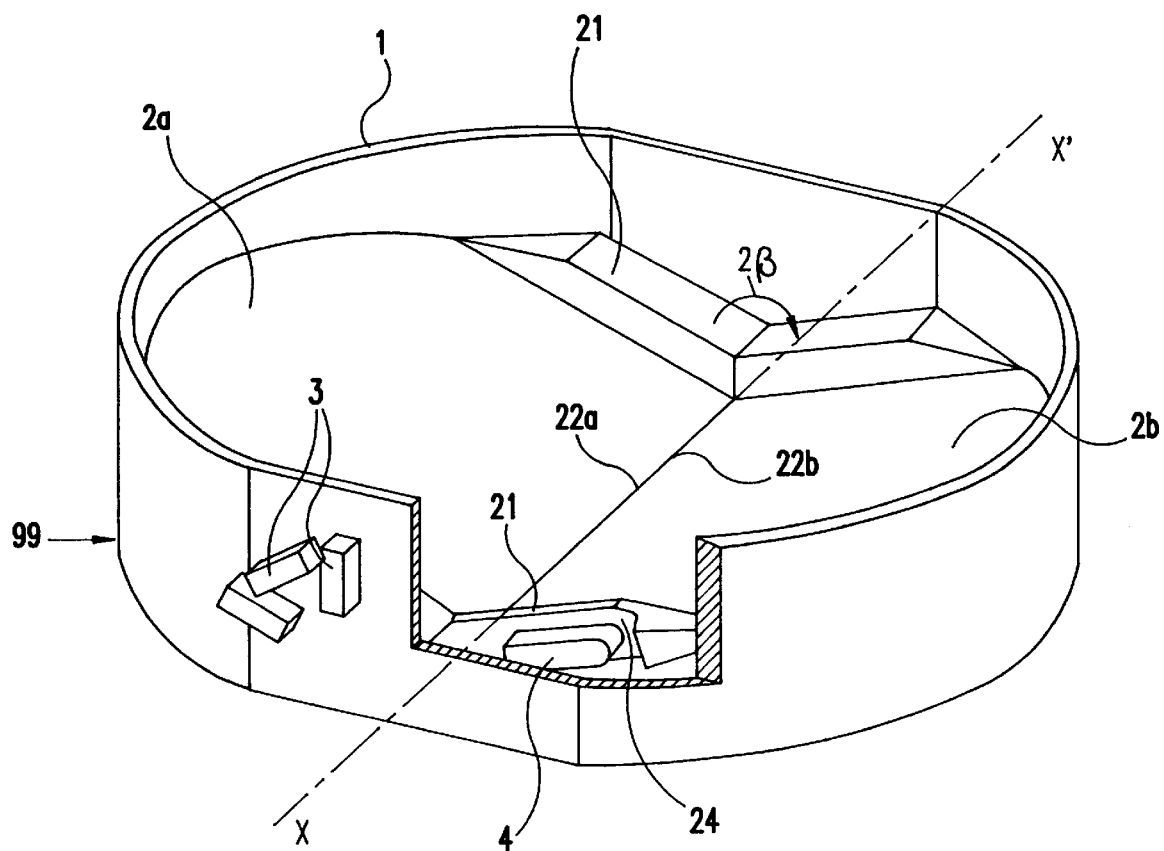
FIGS. 3a, 3b and 3c are a perspective, a cross section and a top view, respectively, of a closed valve equipped with one embodiment of the activating system of the invention.

In the embodiment shown as a cutaway in FIG. 3a, the mobile magnetic element 4 is integrally fixed in a housing 24 created laterally in the boss 21. The housing 24 is itself sealed off in a leaktight manner by a welded cap (not shown), thus enclosing the element 4.

At least as far as the bosses 21 are concerned, the flaps 2a, 2b are preferably made of a hemocompatible titanium alloy. This metal has the further advantage of being light and strong and of permitting both the machining of the housings 24 and the welding of the cap. Also, because of its strength, it enables the flaps to be made thinner than the existing ones that are made of traditional materials (for example pyrocarbon), thereby making it possible to free a greater opening area and hence to reduce the pressure loss across the valve. However, the activating system is compatible with any other hemocompatible material (ceramics, metal alloys, pyrolytic carbon, etc.).

Figure 9:
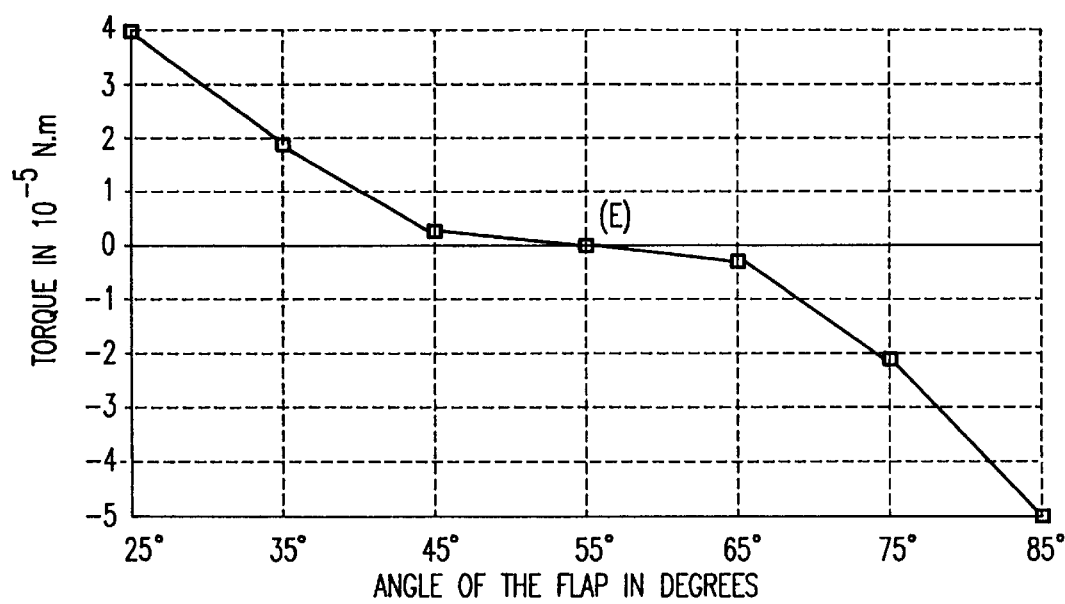
FIGS. 9, 10 and 11 are graphs showing the variations in magnetic restoring torque corresponding to the magnetic configurations of FIGS. 6, 7 and 8, respectively.

The respective magnetic fields of the fixed elements 3 and mobile elements 4 are determined in such a way that their reciprocal influence can control the movements of the flap. In particular, when the blood pressure is identical on either side of the valve 99, an equilibrium position E of the flaps 2a, 2b is created. The flaps are returned to this stable equilibrium position E at all times by a force which produces a magnetic torque varying as a function of the angular position of said flaps. The laws and the graphs of the variations in magnetic restoring torque are determined so as to minimize the reverse blood flow without increasing the pressure loss across the valve. Furthermore, the graph of FIG. 9 shows that for the embodiment described, restoring torques, are independent on either side of the equilibrium position E shown in FIGS. 4a, 4b and 4c. The maximum torque is between $10^{-3}$ and $10^{-5}$ N.m. Equilibrium position E corresponds to a zero magnetic torque and represents an intermediate opening of the flaps, in this case halfway between the closed angular position (FIGS. 3a to 3c) and fully open angular position (FIGS. 5a to 5c). This intermediate opening corresponds in general to an angle 2 β of between 60° and 140° between the flaps 2a, 2b, the positions of the flaps being at all times symmetrical relative to the diametral plane D passing through the axis XX' and disposed at right angles to basal plane S. The equilibrium position E of the flaps corresponds here to an angle α of 55° relative to the basal plane S of the seat 1 (cf. FIG. 9).

In FIGS. 5a, 5b and 5c the valve is shown with the flaps 2a, 2b in the fully open position. In this position the two flaps 2a, 2b are orientated along planes which are parallel both to one another and to the diametral plane D.

In the closed position (FIG. 3a) and in the fully open position (FIG. 5a), the mobile magnetic element 4 carried by the flap 2a, 2b is located exactly parallel to and opposite one of the extreme fixed magnetic elements 3.

In the half-open position E corresponding to equilibrium, the mobile magnetic element 4 is orientated opposite but perpendicular to the interposed fixed magnetic element 3.

The first and second magnetic fields produced respectively by the mobile magnetic element 4 and by the magnetic elements 3 depend of course on the respective geometry and the relative positions of said elements 3, 4 and on their directions of magnetization.

Figure 6:
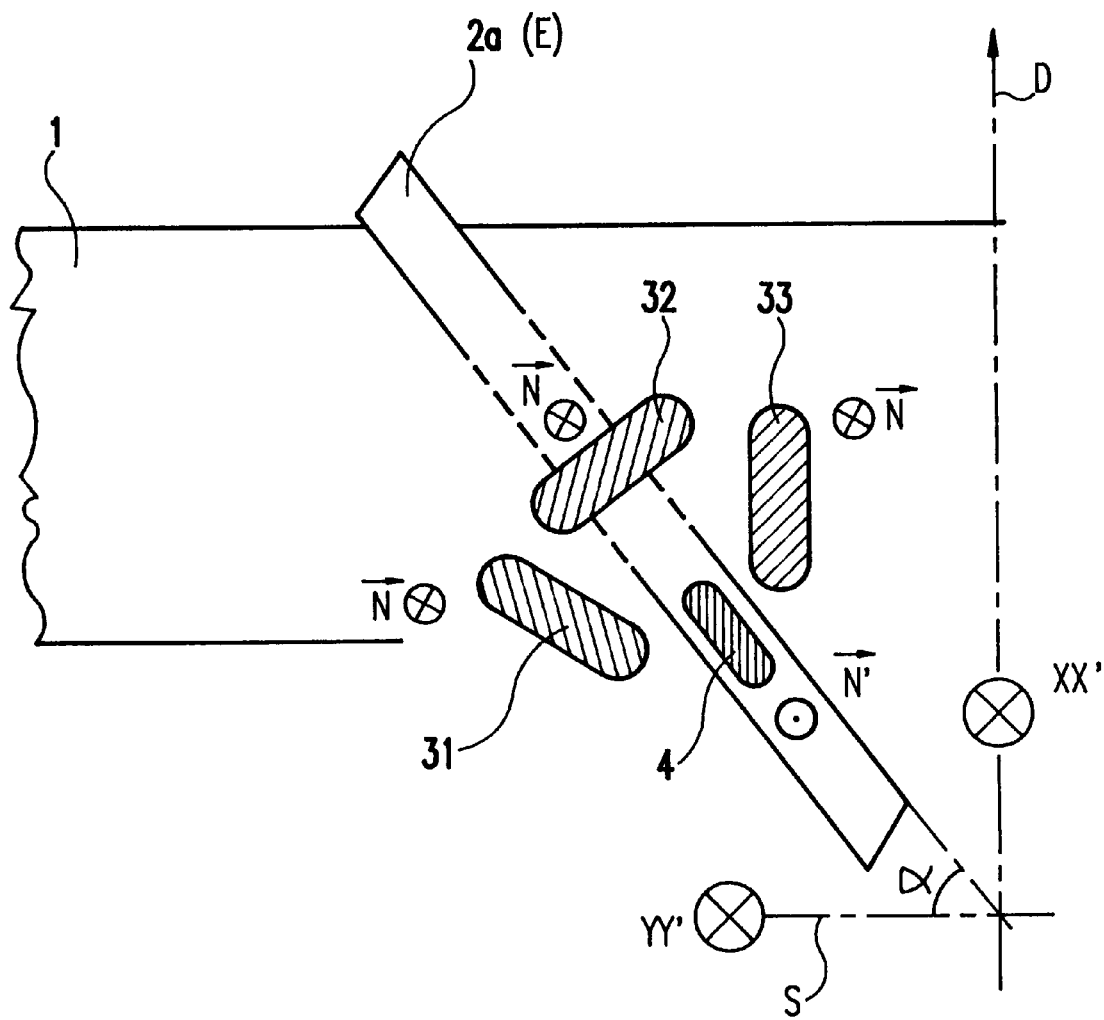
FIGS. 6, 7 and 8 show some of the various possible magnetic configurations for the activating system of the invention.
Figure 7:
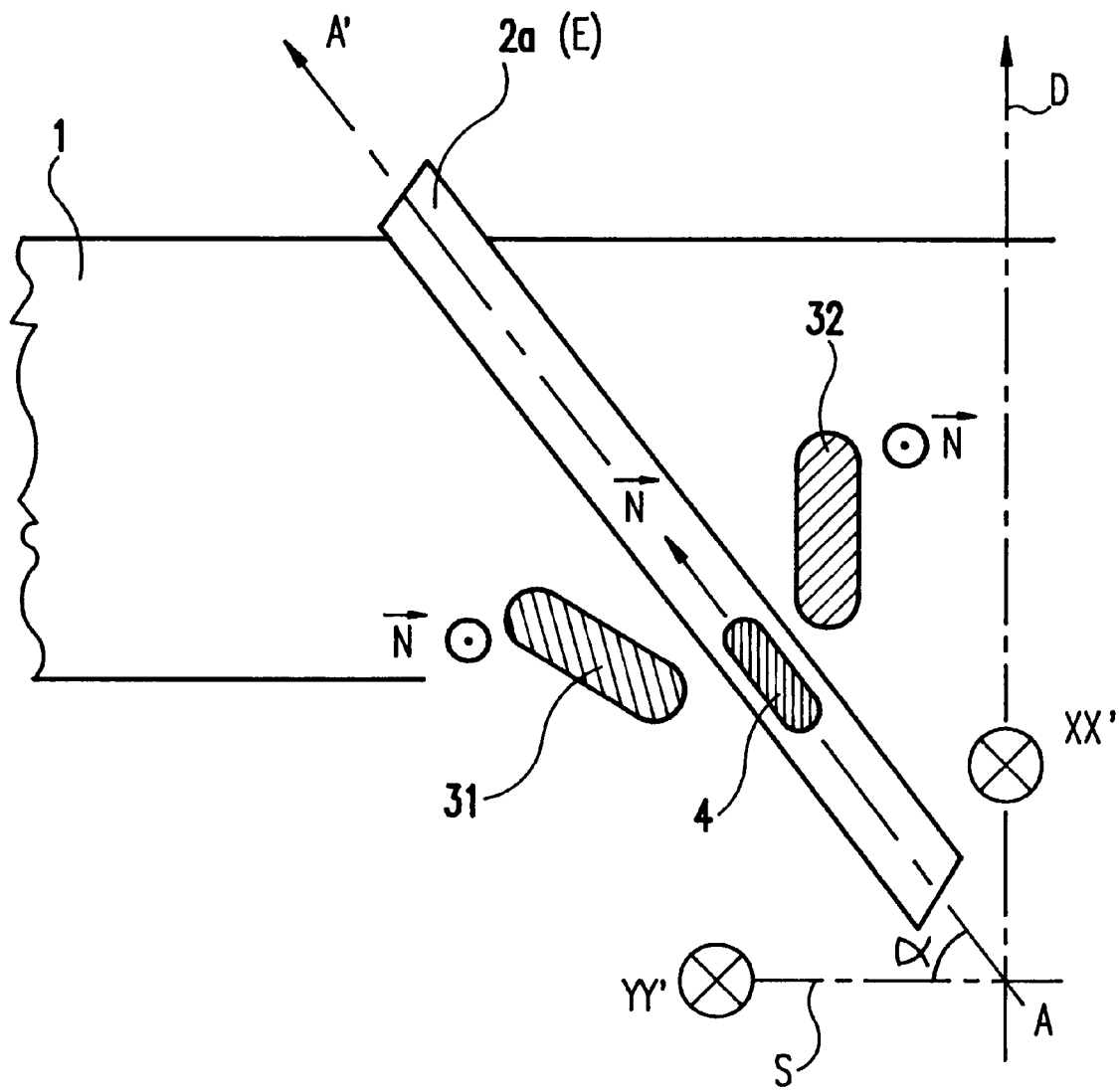
Figure 8:
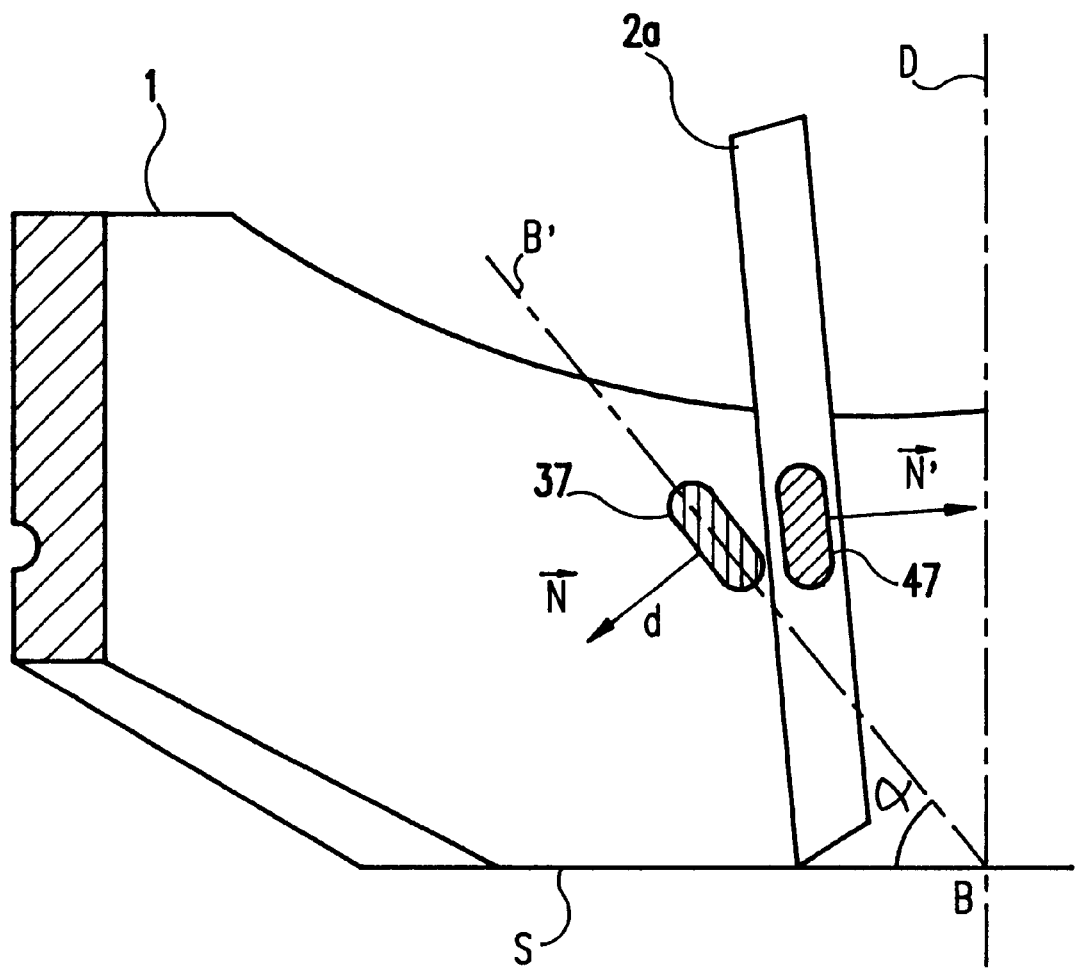

FIGS. 6, 7 and 8 show only some of the various magnetic configurations of the activating system of the invention. Other configurations are feasible and make it possible, as here, to obtain variations in the restoring torque which minimize the reverse blood flow without increasing the pressure loss across the valve 99.

Figure 4A:
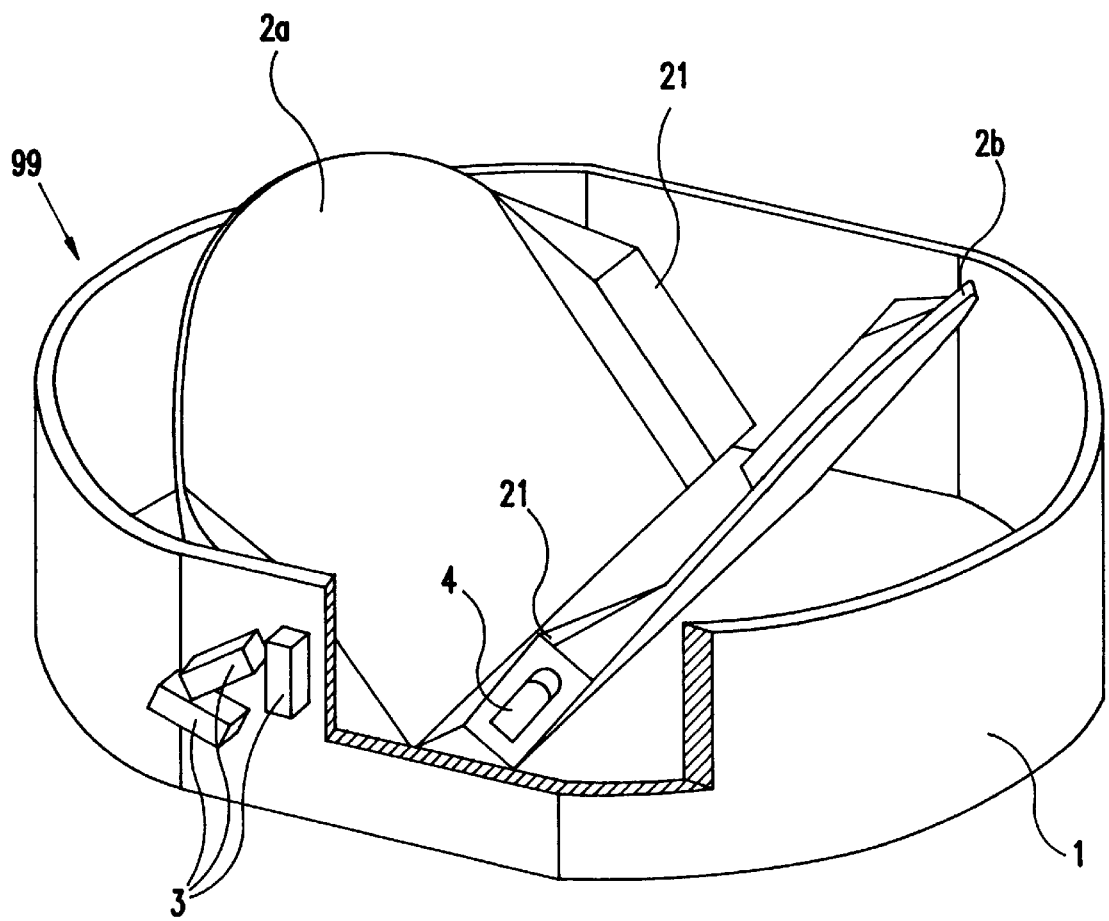
FIGS. 4a, 4b and 4c are a perspective, a cross section and a top view, respectively, of the valve of FIGS. 3a, 3b and 3c in the intermediate equilibrium position.
Figure 5A:
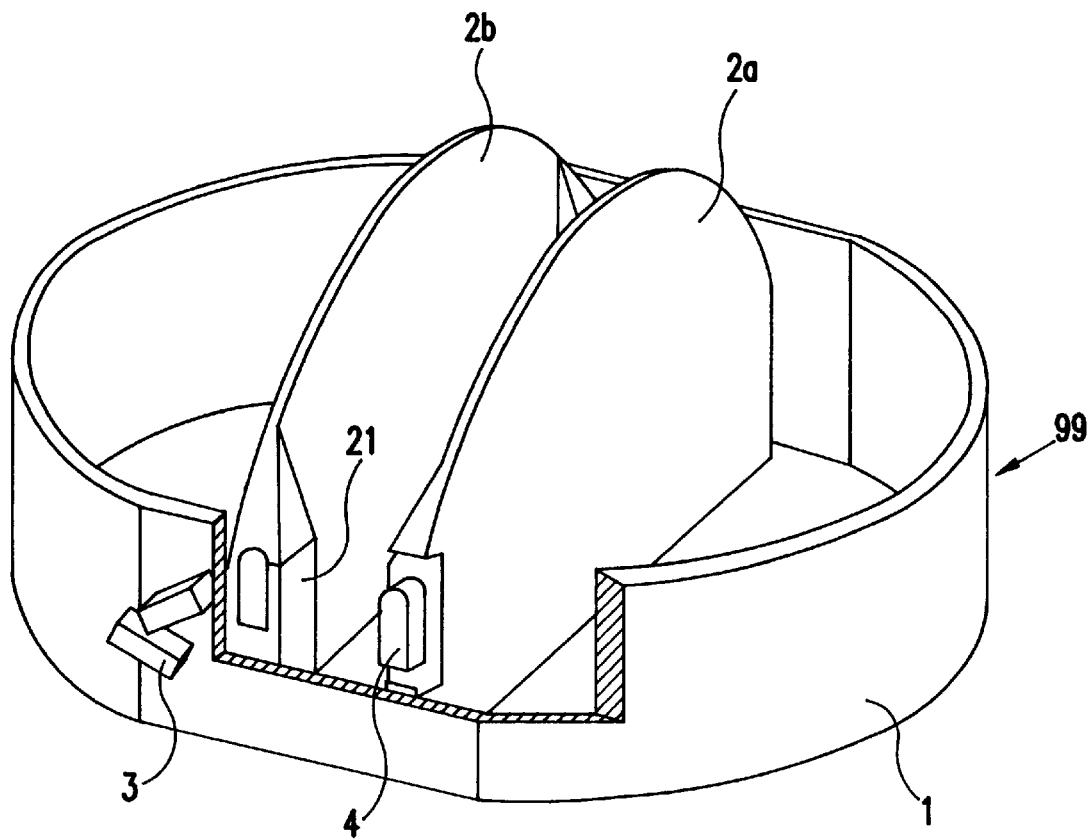
FIGS. 5a, 5b and 5c are a perspective, a cross section and a top view, respectively, of the valve of FIGS. 3a, 3b and 3c in the fully open position.
Figure 5B:
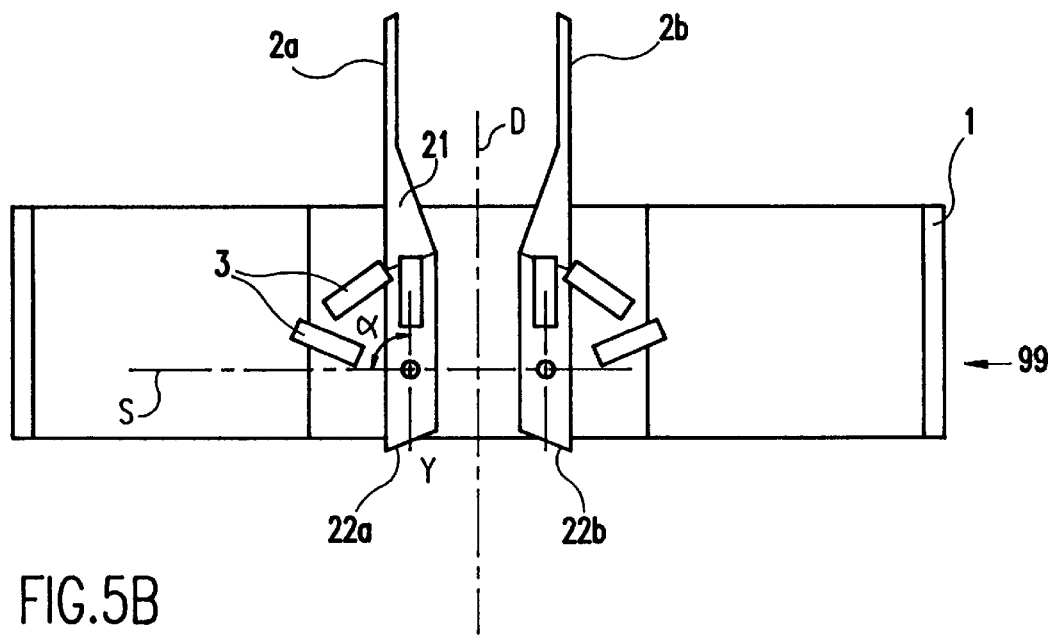
Figure 5C:
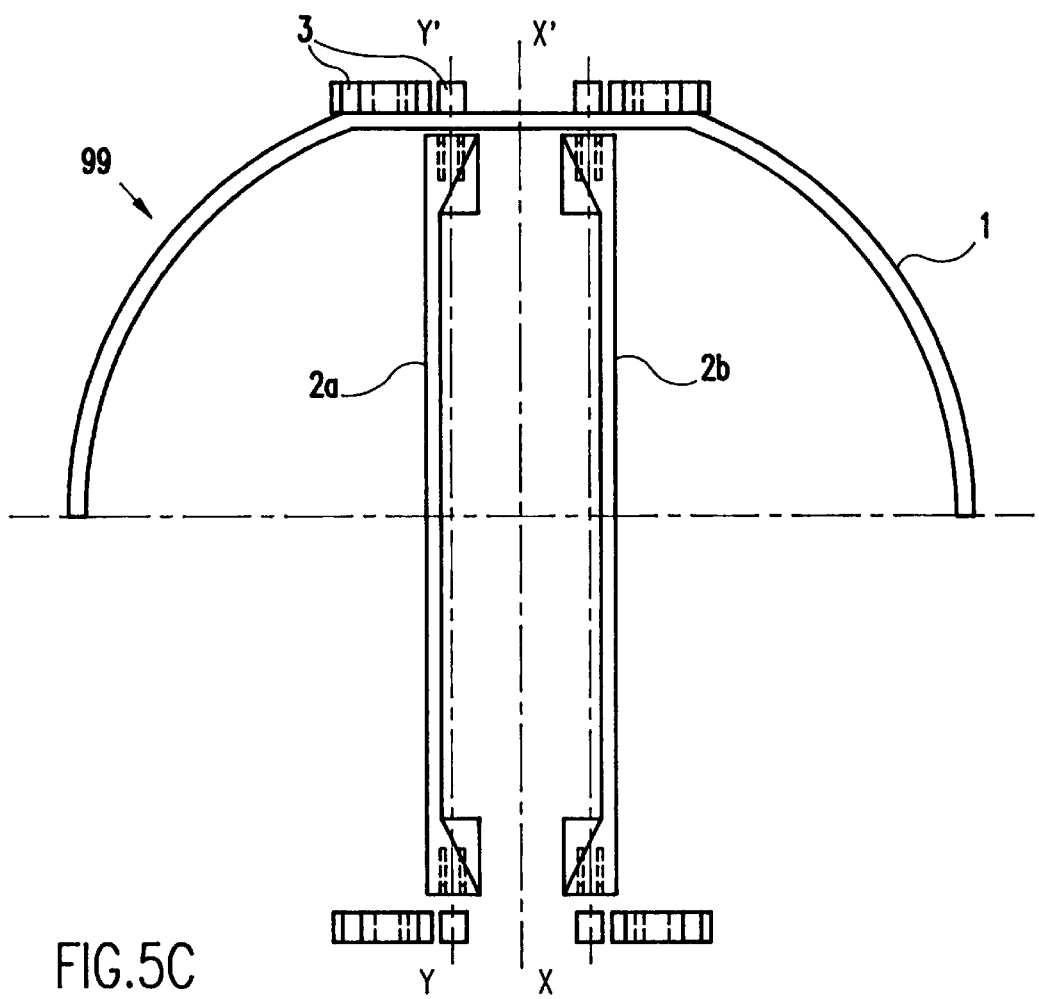

The magnetic configuration with three fixed magnets 3 and one mobile magnet 4 per flap, corresponding to the embodiment of FIGS. 3a, 4a and 5a, is shown in FIG. 6 in the equilibrium position E.

In general the magnetization vector is always directed towards the magnetic north of the magnet in question.

In the configuration shown, the magnetization vectors N of the fixed magnets 31, 32, 33 are orientated positively along the axis of articulation YY', i.e. from Y to Y'.

The magnetization vector N' of the mobile magnet 4 is also orientated parallel to the axis of articulation, but in the opposite direction, i.e. from Y' to Y.

The intensity of the magnetic field produced by the interposed fixed magnet 32 (and hence the value of its vector N) is less than that of the other fixed magnets 31 and 33. As the pivoting of the flap 2a does not modify the orientation of the magnetic field produced by the mobile magnet 4 (the magnetization vector N' remaining orientated along X'X during this pivoting), a torque is automatically created which tends to align the mobile magnet 4 with the interposed fixed magnet 32, returning the flap 2a to the equilibrium position E.

Figure 3B:
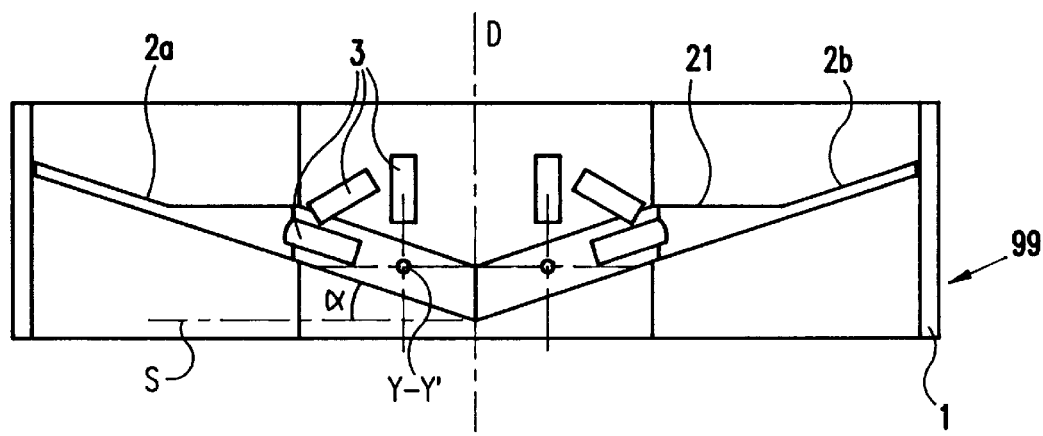
Figure 3C:
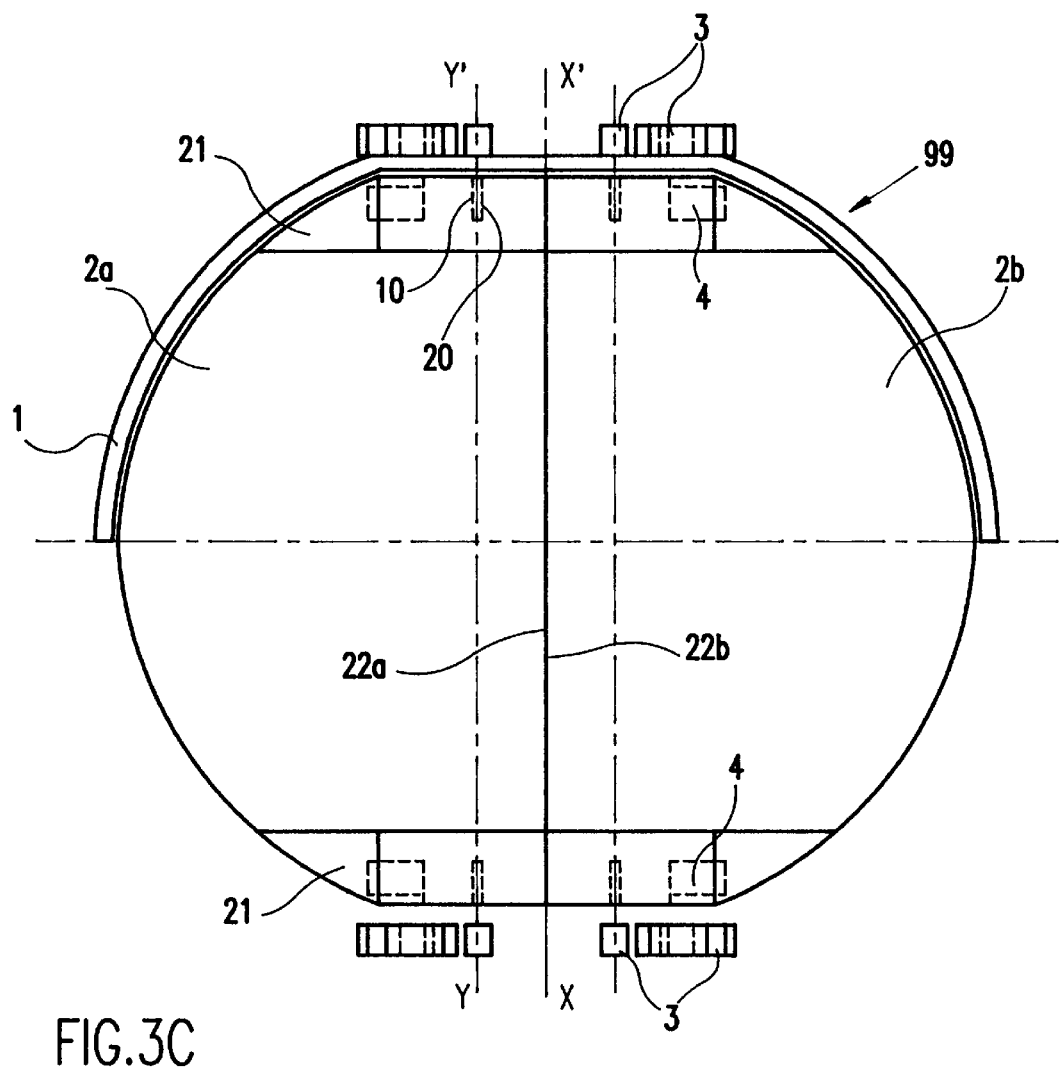
Figure 4B:
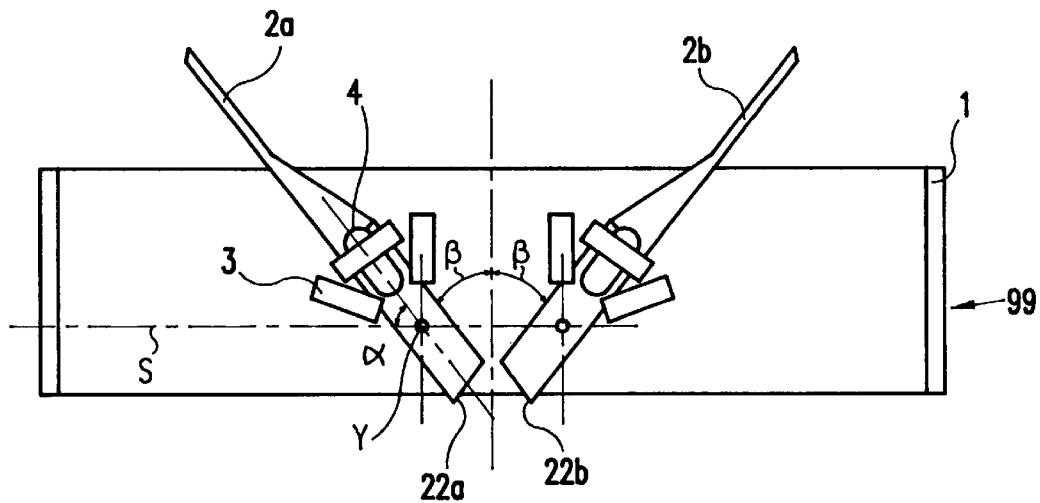
Figure 4C:
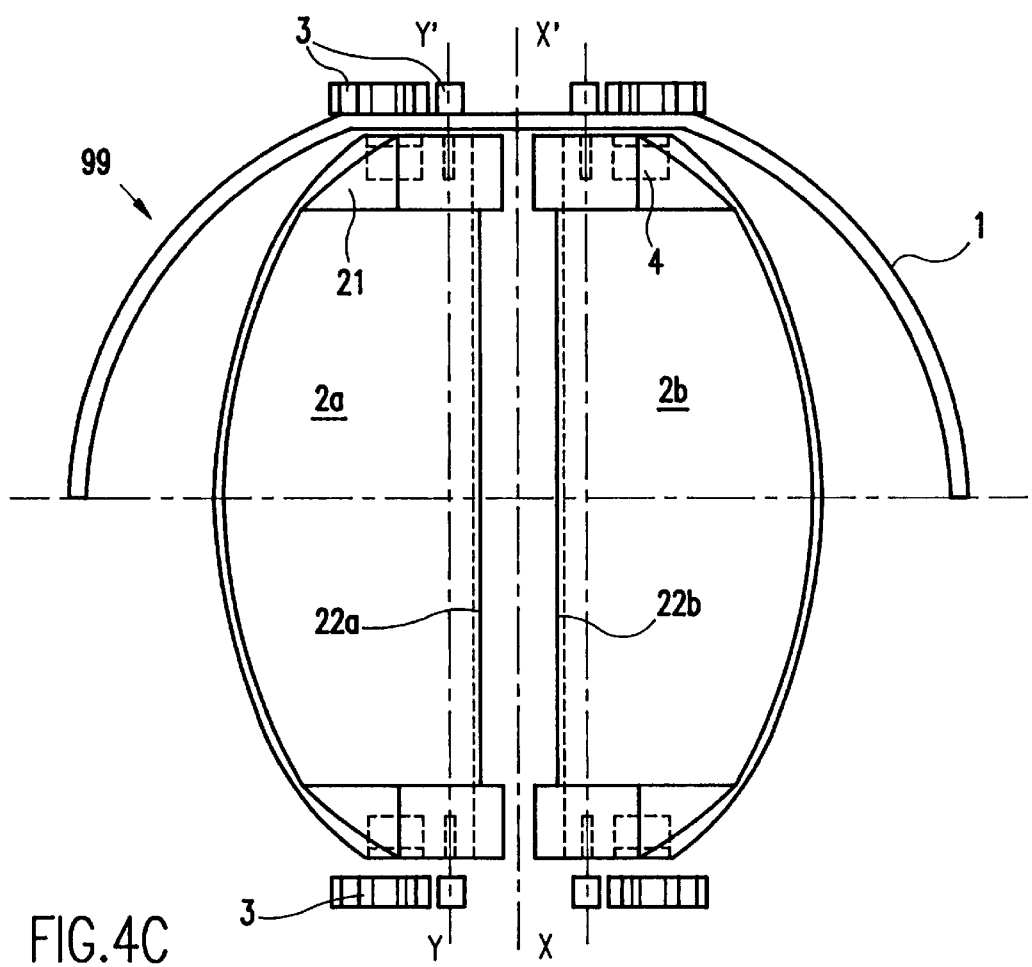

FIG. 9 shows the graphs of the variation in magnetic torque as a function of the angle α of the flap relative to the basal plane S of the seat 1 (cf. FIGS. 3b, 4b and 5b). The fully open position corresponds to an angle α of 85°. the equilibrium position E to an angle α of 55° and the closed position to an angle α of 25°.

The magnetic restoring torque applied from the closed position to the magnetic equilibrium position E gives the flap an impetus to open it when the pressure difference on either side of the valve is zero, and guides it to its magnetic equilibrium position E. Thus, even if the flow rate is very low, the flaps open symmetrically during the downstream flow phase, at least to 55°, thereby providing the blood with a large cross section of flow and guaranteeing a minimum pressure loss. The remainder of the opening path (from 55° to the fully open position) takes place without a substantial loss of energy for the flow, because the magnetic forces are very weak compared with the hydraulic forces.

The restoring torque applied from the fully open position to the magnetic equilibrium position E makes it possible to initiate the movement and then to guide the flap to is magnetic equilibrium position at the moment when the pressure difference across the valve inverts. From the latter position the movement of the flap to its closed position is very rapid because the flap presents the fluid with a large bearing surface, minimizing the reverse flow. The flap then remains closed, ensuring the same level of leaktightness as a passive valve of the same profile until the start of the next cycle.

This example of magnetic assistance corresponds well to the functional demands of a mitral valve prosthesis.

It can be seen from FIG. 9 that the graph of the flap closing torque for values of α between 55° and 85° is different from the graph of the opening torque for values of α between 55° and 25°. In fact, the graphs are only symmetrical on either side of the equilibrium position E for values of a between 35° and 75°. The curves differ beyond these values for the very reason that the laws governing the variations in torque for opening and closing are mutually independent.

FIG. 7 shows a magnetic configuration with two fixed magnets 31, 32 and one mobile magnet 4.

The magnetization vectors N of the fixed magnets 31, 32 are orientated along the axis of articulation Y'Y, i.e. in the direction from Y' to Y, namely in the opposite direction to the configuration of FIG. 6.

The magnetization vector N' of the mobile magnet 4 is orientated along the longitudinal axis AA' of the flap 2a, which forms an angle α with the basal plane S of the seat 1, and toward the extreme free edge of said flap. When the flap 2a approaches its fully open position, the mobile magnet 4 is repelled by the fixed magnet 32, creating a restoring torque towards the equilibrium position E, shown in FIG. 7, where the flap forms an angle α of 35° with the basal plane S.

The same phenomenon occurs when the flap 2a approaches its closed position, due to interaction of the mobile magnet 4 with the fixed magnet 31. The magnetic restoring torque applied from the closed position to the magnetic equilibrium position guarantees a minimum opening of the flap to 35° during the downstream flow phase of the blood.

The restoring torque applied from the fully open position to the magnetic equilibrium position E makes it possible to initiate and then to guide the flap to this position at the moment when the pressure difference across the valve inverts. From the latter position the movement of the flap to its closed position is virtually instantaneous because the flap presents the fluid with a large bearing surface and it now only has an angular distance of 10° to cover. The magnetic restoring torque acting towards the magnetic equilibrium position still exists when the flap forms an angle of 90° with the basal plane S of the seat, so the valve profile can allow the flaps to open to 90° so as to minimize the pressure loss across the valve when the flow rate is high, without having to fear an increase in the reverse flow.

This example of magnetic assistance corresponds well to the functional demands of an aortic valve prosthesis.

Figure 10:
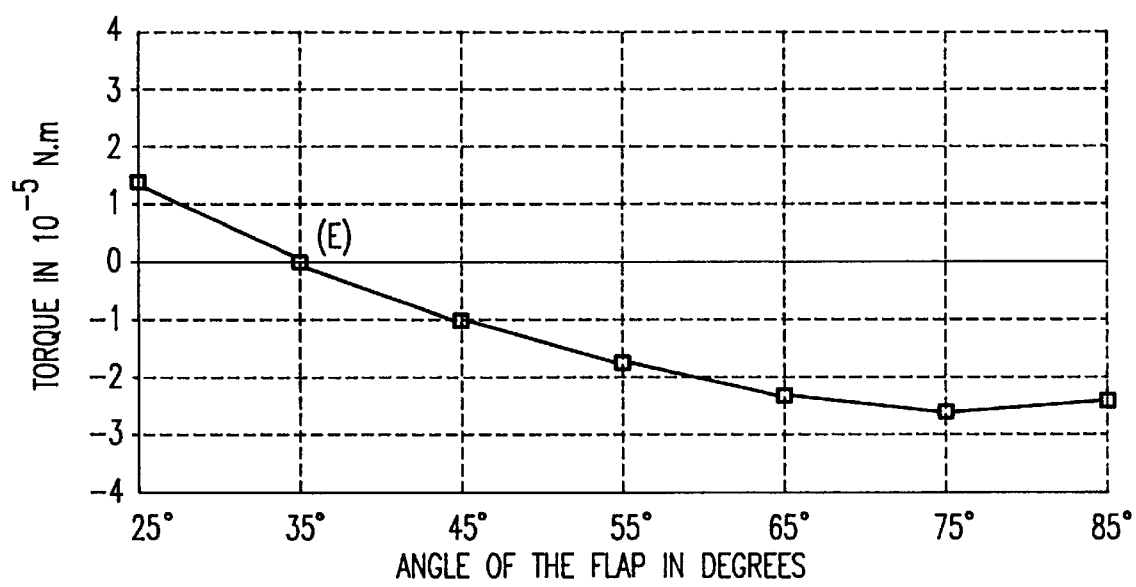

FIG. 10 shows the graph of the variations in restoring torque as a function of the angular position of the flap for the magnetic configuration shown in FIG. 7.

The equilibrium position E is situated at α=35° relative to the plane S, so in this case it does not correspond to the half-open position. It is clear from this graph that there is no symmetry in the law governing the variation in magnetic torque on either side of the equilibrium position E. Therefore, this variation does not necessarily obey the same rules for the opening phase as for the closing phase, but it must not under any circumstances display sudden changes in slope.

FIG. 8 shows a magnetic configuration with one fixed magnet 37 and one mobile magnet 47. The magnetization vector N of the fixed magnet 37 is orientated in a direction d, whereas the magnetization vector N' of the mobile magnet 47 is orientated along the normal to the top side of the flap 2a. Consequently the mobile magnet 47 tends to move in such a way that its magnetization vector N' is parallel to the magnetization vector N of the fixed magnet 37, but pointing in the opposite direction, so as to cause looping of the magnetic field lines. This amounts to placing the fixed magnet 37 and mobile magnet 47 opposite one another. This phenomenon creates a magnetic torque which returns the flap 2a to an equilibrium position E, represented by the plane BB' in FIG. 8. Here the flap 2a is in its magnetic equilibrium position E, when it forms an angle α of 45° with the basal plane S of the seat. The magnetic restoring torque applied from the closed position to the magnetic equilibrium position guarantees a minimum opening of the flap to 45° during the downstream flow phase of the blood. The restoring torque applied from the fully open position to the magnetic equilibrium position makes it possible to guide the flap 2a to this position at the moment when the pressure difference across the valve inverts, thereby minimizing the reverse flow.

This example of magnetic assistance can satisfy the functional demands of either an aortic or a mitral valve prosthesis, but will constitute a less optimal solution by virtue of being less specific.

Figure 11:
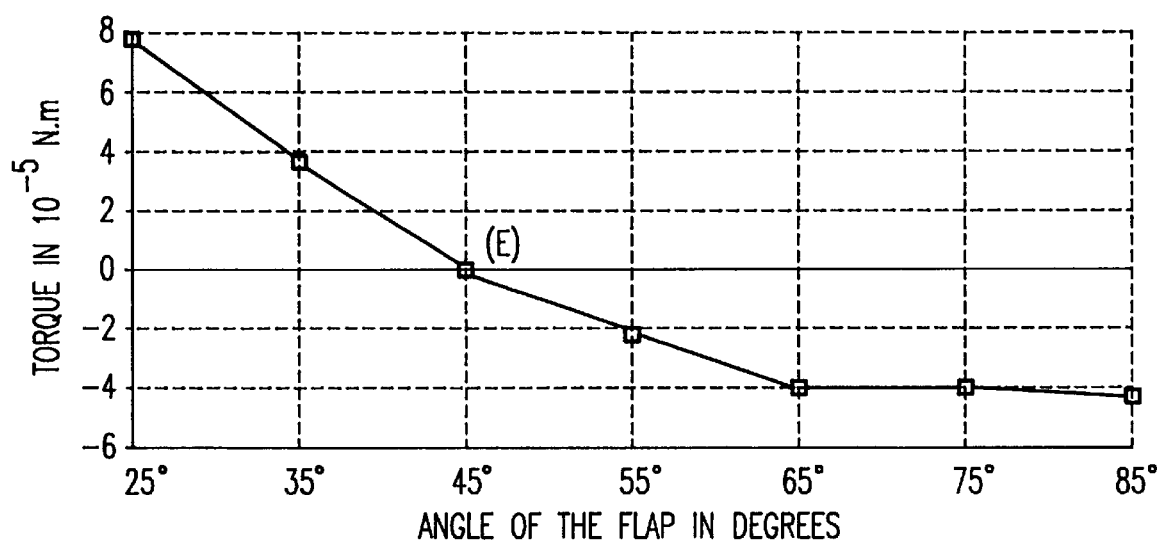

It is of course possible, still according to the invention, to obtain the graphs of variations of FIGS. 9, 10 and 11 with different configurations from those shown in FIGS. 6, 7 and 8, or other configurations, by choosing particular geometries and/or relative positions and/or magnetizations for the fixed magnets 3 and mobile magnet 4.

Furthermore, it is also possible to envisage creating a reciprocal influence between the activating system of the flap 2a and the activating system of the flap 2b.

In this embodiment the activating system operates only under the influence of the mobile magnetic elements. In this case the fixed magnetic elements of the seat are then non-existent or inactive or else they produce a negligible influence compared with that produced by the mobile magnetic elements.

Although the present invention has been described in relation to particular embodiments thereof, many other variations and modifications and other uses will become apparent to those skilled in the art. It is preferred, therefore, that the present invention be limited not by the specific disclosure herein, but only by the appended claims.

We claim:

1. An activated heart valve, comprising:
   a heart valve which comprises
      a seat, and
      at least one flap pivotally mounted on said seat; and
   an activating system which comprises at least one respective mobile magnetic element connected with each said at least one flap, and at least one fixed magnetic element mounted to said seat, said fixed and said mobile magnetic elements producing magnetic fields that interact to generate a force which urges said at least one flap towards an equilibrium position when blood pressure is identical on either side of said valve, wherein said equilibrium position corresponds to a fixed table intermediate open position between a fully open position and a fully closed position of said at least one flap.

2. An activated heart valve according to claim 1, wherein said force varies as a function of a position of said at least one flap so as to minimize reverse blood flow and pressure loss across the valve during movement between a fully open position and a fully closed position.

3. An activated heart valve according to claim 2, wherein variations in said force occur asymmetrically from one side to the other side of the equilibrium position.

4. An activated heart valve according to claim 3, wherein said force produces a magnetic torque on said at least one flap, said force having a maximum value between $10^{-3}$ and $10^{-5}$ N.m.

5. An activated heart valve according to claim 1, wherein said magnetic fields are determined in such a way that said at least one flap pivots relative to said seat with a minimum amount of friction.

6. An activated heart valve according to claim 1, wherein said fixed and said mobile magnetic elements produce a first magnetic field and a second magnetic field, respectively said first and second magnetic fields producing repulsive magnetic forces between said mobile magnetic element and said fixed magnetic element.

7. An activated heart valve according to claim 6, wherein said repulsive magnetic forces have an intensity of at most $10^{-1}$ N.

8. An activated heart valve according to claim 1, wherein said seat includes a thickness and said at least one fixed magnetic element is integrated into said thickness of said seat.

9. An activated heart valve according to claim 1, wherein each said flap includes a respective thickness and said at least one mobile magnetic element is integrated in a leak-tight manner into said respective thickness of each said flap.

10. An activated heart valve according to claim 1, wherein said at least one fixed magnetic element comprises three fixed magnetic elements.

11. An activated heart valve according to claim 1, wherein said at least one fixed magnetic element comprises two fixed magnetic elements.

12. An activated heart valve according to claim 11, wherein said two fixed magnetic elements are disposed on said seat in such a way as to define said fully open and said fully closed positions of each said flap.

13. An activated heart valve according to claim 10, wherein said three fixed magnetic sections are arranged in a ring around an axis of articulation of each said flap.

14. An activated heart valve according to claim 1, wherein at least one of said fixed or mobile magnetic elements is a permanent magnet.

15. An activated heart valve according to claim 14, wherein at least one of said fixed or mobile magnetic elements is a rare earth permanent magnet made from a combination of samarium and cobalt or combination of neodymium, iron and boron.

16. An activated heart valve according to claim 1, wherein said at least one flap comprises a hemocompatible material which enables said at least one mobile magnet to be incorporated therein without modification of the magnetic characteristics of said at least one mobile magnet.

17. An activated heart valve according to claim 1, wherein said at least one flap comprises two flaps which are activated only by reciprocal influence of said respective mobile magnetic elements of each flap.

18. An activated heart valve according to claim 16, wherein said at least one flap is constructed of a hemocompatible titanium alloy.

19. An activated heart valve according to claim 1, wherein said force produces a magnetic torque on said at least one flap, said force having a maximum value between $10^{-3}$ and $10^{-5}$ N.m.

20. An activated heart valve according to claim 2, wherein said magnetic fields are determined in such a way that said at least one flap pivots relative to said seat with a minimum amount of friction.

21. An activated heart valve according to claim 2, wherein said fixed and said mobile magnetic elements produce a first magnetic field and a second magnetic field, respectively, said first and second magnetic fields producing repulsive magnetic forces between said mobile magnet element and said fixed magnetic element.

22. An activated heart valve according to claim 10, wherein said three fixed magnetic elements are disposed on said seat in such a way as to define said equilibrium position, said fully open position and said fully closed position of said at least one flap.

23. An activated heart valve according to claim 17, wherein each flap is constructed of a hemocompatible titanium alloy.

* * * * *